US00PP12921P2

(12) United States Plant Patent
Fruehwirth

(10) Patent No.: US PP12,921 P2
(45) Date of Patent: Sep. 3, 2002

(54) POINSETTIA PLANT NAMED 'ECKAILEEN'

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 76 days.

(21) Appl. No.: 09/779,345

(22) Filed: Feb. 9, 2001

(51) Int. Cl.[7] ..... A01H 5/00
(52) U.S. Cl. ..... Plt./303
(58) Field of Search ..... Plt./303

*Primary Examiner*—Bruce R. Campell
*Assistant Examiner*—Annette Para
(74) *Attorney, Agent, or Firm*—C. A. Whealy

(57) ABSTRACT

A new and distinct cultivar of Poinsettia plant named 'Eckaileen', characterized by its inflorescences with recurved red and dark pink bi-colored flower bracts; dark green-colored recurved leaves with burgundy-colored petioles; compact, uniform and upright plant habit; natural season flower maturity date is December 5 for plants grown in Encinitas, Calif.; reponse time, about 10 weeks; and excellent post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Eckaileen'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia is a naturally-occurring whole plant mutation of the Poinsettia cultivar Windark, disclosed in U.S. Plant patent application Ser. No. 09/087,917. The new Poinsettia was discovered and selected by the Inventor as a single flowering plant within a population of plants of the parent cultivar in a controlled environment in Encinitas, Calif., in December, 1998. The selection of this plant was based on its attractive flower bract colors and good plant form and substance.

Asexual reproduction of the new Poinsettia by terminal cuttings taken at Encinitas, Calif., since December, 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckaileen'. These characteristics in combination distinguish 'Eckaileen' as a new and distinct cultivar.

1. Inflorescences with recurved red and dark pink bi-colored flower bracts.
2. Dark green-colored recurved leaves with burgundy-colored petioles.
3. Compact, uniform and upright plant habit.
4. Natural season flower maturity date is December 5 for plants grown in Encinitas, Calif.; response time, about 10 weeks.
5. Excellent post-production longevity.

Plants of the new Poinsettia differ primarily from plants of the mutation parent, the cultivar Windark, in flower bract coloration as flower bracts of plants of the cultivar Windark are solid red in color.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph on the first sheet comprises a side perspective view of three typical plants of 'Eckaileen' planted in a single container.

The photograph at the top of the second sheet comprises a top perspective view of three typical plants of 'Eckaileen' planted in a single container.

The photograph at the bottom of the second sheet is a close-up view of typical leaves and flower bracts of 'Eckaileen' (top) and 'Windark' (bottom). Plants used in the photographs were about 19 weeks old.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 24° C., night temperatures about 19° C., and light levels about 4,000 foot-candles. Three plants were grown in 16.5-cm pots as single-stem plants and flowered under naturally lengthening nyctoperiods during the fall. Plants used for the description were about 19 weeks old.

In the following description, color references are made to The Royal Horticultural Society Colour Chart except where general terms of ordinary dictionary significance are used.

Botanical classification: *Euphorbia pulcherrima* Willd. cultivar Eckaileen.

Parentage: Naturally-occurring whole plant mutation of *Euphorbia pulcherrima* Willd. cultivar Windark, disclosed in U.S. Plant patent application Ser. No. 09/087,917.

Propagation:

*Type cutting.*—Terminal cuttings.

*Time to initiate roots.*—About 10 days at 20 to 22° C.

*Time to develop roots.*—About 28 days at 20 to 22° C.

*Rooting habit.*—Thick, fibrous and freely-branching.

Plant description:

*Plant form.*—Inverted triangle, top of plant rounded; mounding.

*Growth habit.*—Upright, compact and uniform plant habit. Strong, thick stems. Moderate vigor to vigorous.

*Plant height.*—About 26 cm.

*Plant diameter or spread.*—About 33 cm.

*Crop time.*—From unrooted cuttings to a flowering plant in a 16.5-cm container, about 19 weeks are required.

*Stem description.*—Length: About 26 cm. Diameter: About 1.4 cm. Internode length: About 1.25 cm. Stem color: 146A.

*Foliage description.*—Alternate, simple. Quantity of leaves per plant: About 15. Length: About 8 cm. Width: About 7 cm. Shape: Mostly ovate; slightly lobed. Apex: Acuminate. Base: Acute. Margin: Entire. Texture: Mostly glabrous with very slight pubescence on lower surface. Surface: Smooth, rugose; recurved. Color: Young foliage, upper surface: Darker than 147A. Young foliage, lower surface: 147A. Mature foliage, upper surface: Much darker than 147A; venation, 147B. Mature foliage, lower surface: 137A to 137B; venation, 147C. Petiole: Length: About 2.25 cm. Diameter: About 4 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northen Hemisphere. Flower initiation and development can be induced under long nyctoperiod conditions. Response time, about 10 weeks; natural season flower maturity date is December 5 for plants grown in Encinitas, Calif.

*Post-production longevity.*—Plants of the new Poinsettia maintain good substance and bract color for about 4 to 6 weeks under interior conditions and for about 8 weeks under greenhouse conditions.

*Quantity of inflorescences.*—Plants grown as single-stem plants, one inflorescence per plant.

*Inflorescence size.*—Diameter: About 13 cm. Height (depth): About 6.5 cm.

*Flower bracts.*—Quantity of flower bracts per inflorescence: Usually about 22 to 24 bracts per inflorescence. Length, largest bracts: About 10 cm; stalk about 6 mm. Width, largest bracts: About 8.5 cm. Shape: Mostly ovate. Apex: Acuminate. Base: Acute. Margin: Entire. Texture: Glabrous, velvety. Surface: Smooth, rugose, appears ruffled. Orientation: Recurved; inflorescences shaped like a flattened sphere. Color: Developing, upper surface: Ground color, 45A, randomly flecked with 51B. Developing, lower surface: Ground color, 45B to 45C, randomly flecked with 51C. Mature, upper surface: Ground color, 45A to 45B, randomly flecked with 52B; color does not fade with subsequent development. Mature, lower surface: 46B.

*Cyathia.*—Quantity: Usually about 12 per corymb. Diameter of cyathia cluster: About 2.5 by 3 cm. Length: About 1.2 cm. Width: About 5 mm. Shape: Ovate. Color: Immature: 144A. Mature: 145A. Peduncle: Length: About 3 mm. Aspect: Strong, erect. Color: 144B. Stamens: Stamen number: At least 20 per cyathium. Anther shape: Oval. Anther length: About 1 mm. Anther color: 45A. Amount of pollen: Moderate. Pollen color: 9A. Pistils: Not observed. Nectary number: One per cyathia. Nectary color: 14A.

Disease resistance: Resistance to pathogens common to Poinsettias has not been observed on plants grown under commercial conditions.

It is claimed:

1. A new and distinct cultivar of Poinsettia plant named 'Eckaileen', as illustrated and described.

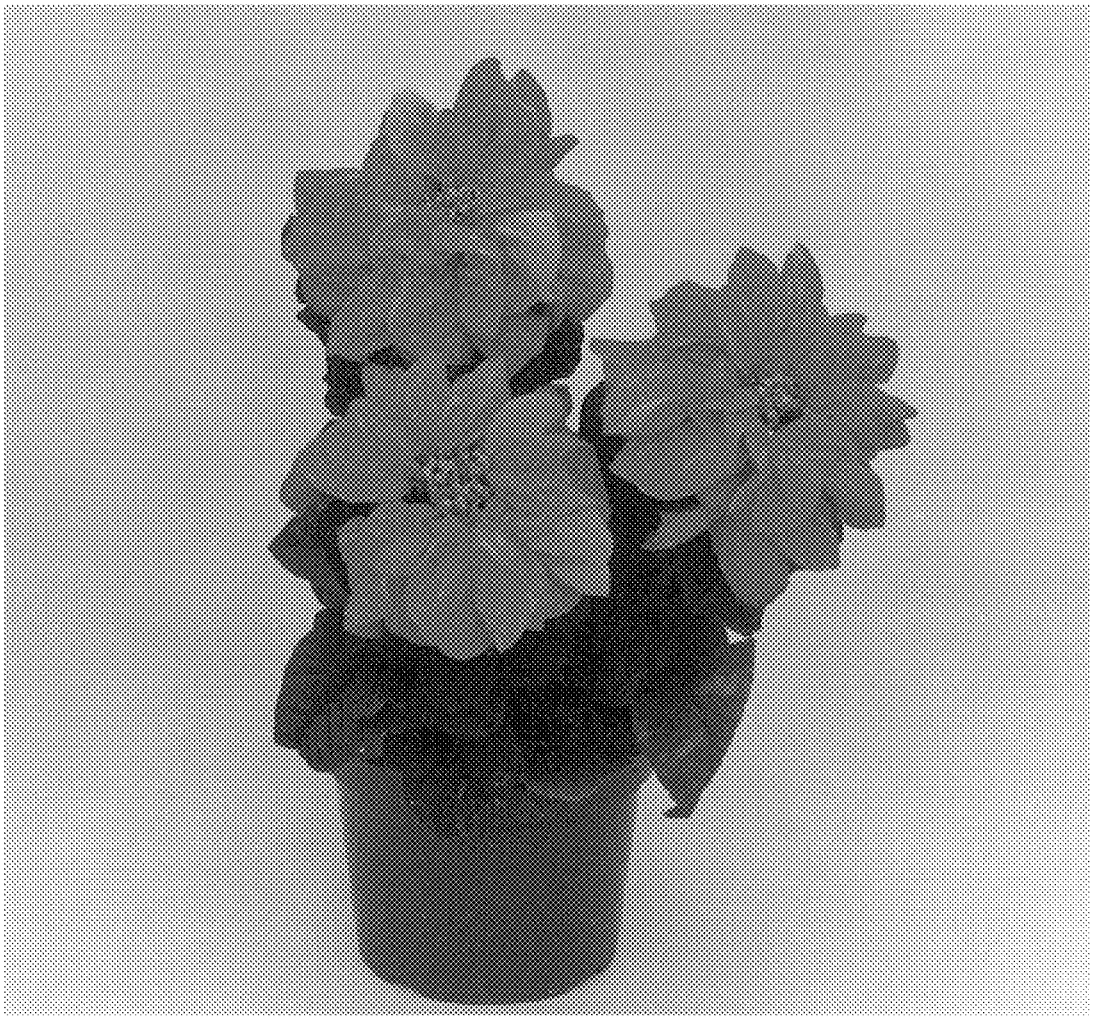

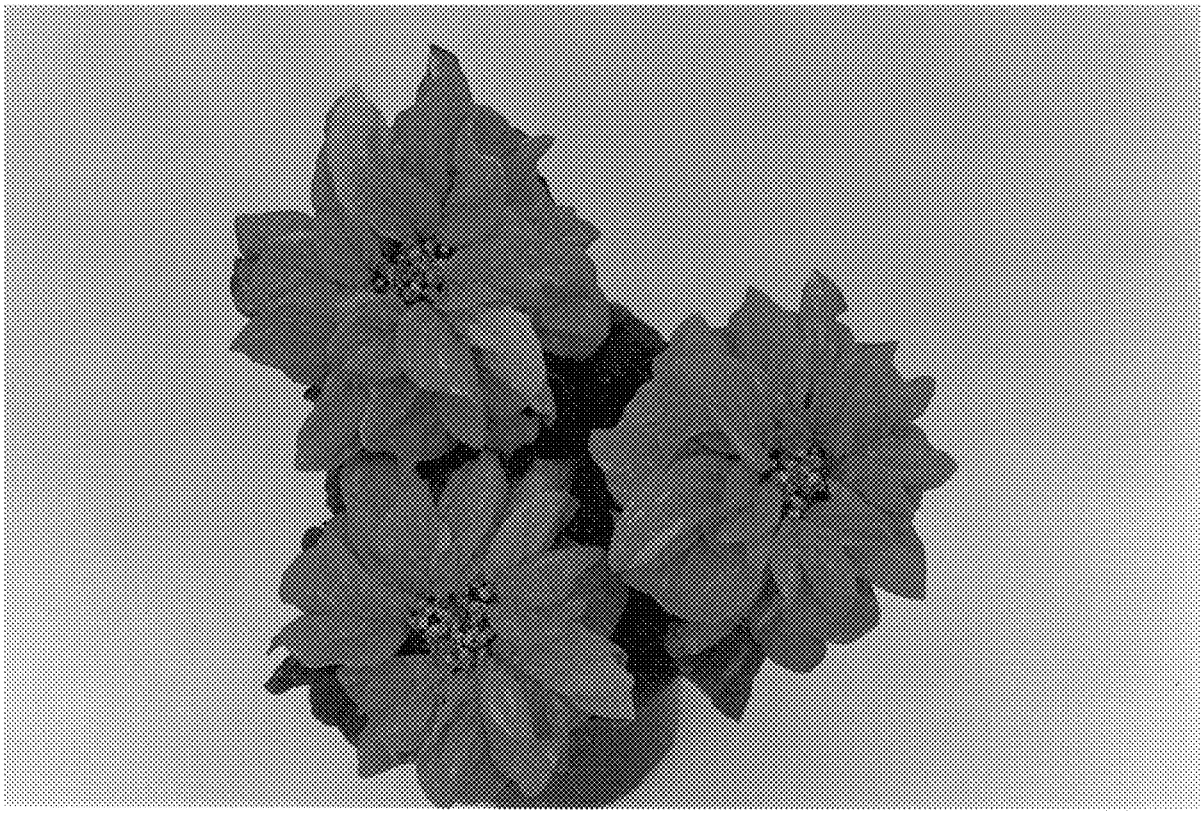
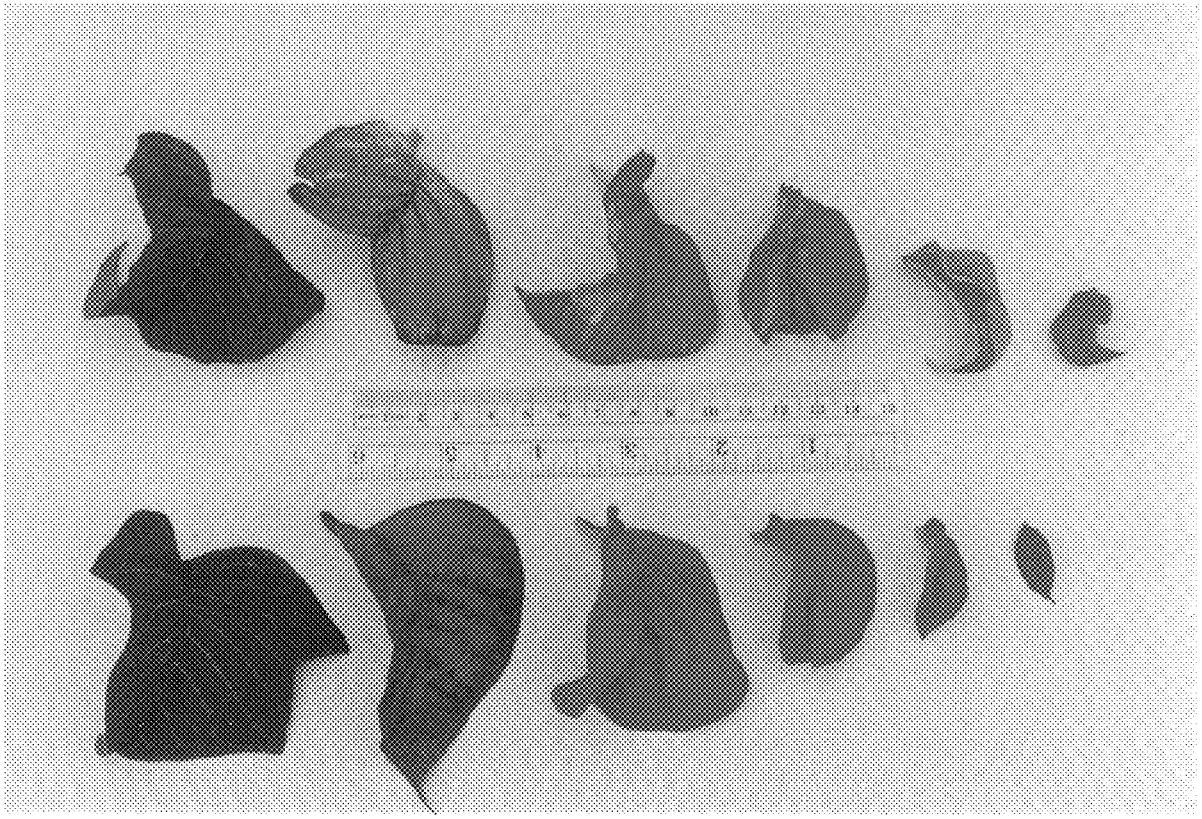

* * * * *